US007189366B2

(12) United States Patent
Krise et al.

(10) Patent No.: US 7,189,366 B2
(45) Date of Patent: Mar. 13, 2007

(54) MOLECULAR TAG READER

(75) Inventors: William F. Krise, Bozeman, MT (US); John L. Sternick, Mansfield, PA (US)

(73) Assignee: The United States of America as represented by the Secretary of the Interior, Washington, DC (US)

( * ) Notice: Subject to any disclaimer, the term of this patent is extended or adjusted under 35 U.S.C. 154(b) by 225 days.

(21) Appl. No.: 09/864,373

(22) Filed: May 25, 2001

(65) Prior Publication Data

US 2002/0182150 A1 Dec. 5, 2002

(51) Int. Cl.
*B01L 3/02* (2006.01)

(52) U.S. Cl. .................. 422/100; 422/68.1; 422/82.05; 422/82.08; 435/287.1; 435/287.3; 435/287.7; 435/288.7

(58) Field of Classification Search ............... 422/68.1, 422/82.05, 82.08, 100, 57–59; 435/4, 6, 435/7.1, 7.9, 283.1, 287.1–287.3, 288.2–288.5, 435/288.7, 808; 436/164, 172, 518, 524, 436/528, 805, 823
See application file for complete search history.

(56) References Cited

U.S. PATENT DOCUMENTS

| | | | | | |
|---|---|---|---|---|---|
| 4,515,889 | A | * | 5/1985 | Klose et al. | 435/4 |
| 5,313,264 | A | * | 5/1994 | Ivarsson et al. | 356/73 |
| 5,571,388 | A | * | 11/1996 | Patonay et al. | 204/461 |
| 5,674,698 | A | * | 10/1997 | Zarling et al. | 435/7.92 |
| 5,804,451 | A | * | 9/1998 | Wang et al. | 436/93 |
| 6,066,448 | A | * | 5/2000 | Wohlstadter et al. | 435/6 |
| 6,086,737 | A | * | 7/2000 | Patonay et al. | 204/461 |
| 6,191,278 | B1 | * | 2/2001 | Lee et al. | 546/41 |
| 6,236,456 | B1 | * | 5/2001 | Giebeler et al. | 356/318 |
| 6,249,085 | B1 | * | 6/2001 | Arai | 313/506 |
| 6,342,395 | B1 | * | 1/2002 | Hammock et al. | 436/518 |
| 6,395,562 | B1 | * | 5/2002 | Hammock et al. | 436/518 |
| 6,397,150 | B1 | * | 5/2002 | Izmailov | 702/20 |
| 6,593,148 | B1 | * | 7/2003 | Narayanan | 436/546 |

OTHER PUBLICATIONS

Baars et al. Ultrasensitive detection of closely related angiotensin I peptides using capillary electrophoresis with near-infrared laser-induced fluorescence detection. Analytical Chemistry, 1999, vol. 71, pp. 667-671.*

Ekong et al. Immunological detection of *Clostridium botulinum* toxin type A in therapeutic preparations. Journal of Immunological Methods, 1995, vol. 180, pp. 181-191.*

* cited by examiner

*Primary Examiner*—Long V. Le
(74) *Attorney, Agent, or Firm*—Mark Homer; Joan Gilsdorf

(57) ABSTRACT

Near infrared molecular assays can be used to detect small quantities of a molecule of interest in vivo or in vitro using laser dyes. A hand-held portable device is provided which can rapidly read small quantities of selected molecular tags in tissues of fish or other animals in the field. The device is composed of four components:

(1) a light source, such as a laser diode;
(2) a sample holder;
(3) an optical system; and
(4) a detector.

9 Claims, 7 Drawing Sheets

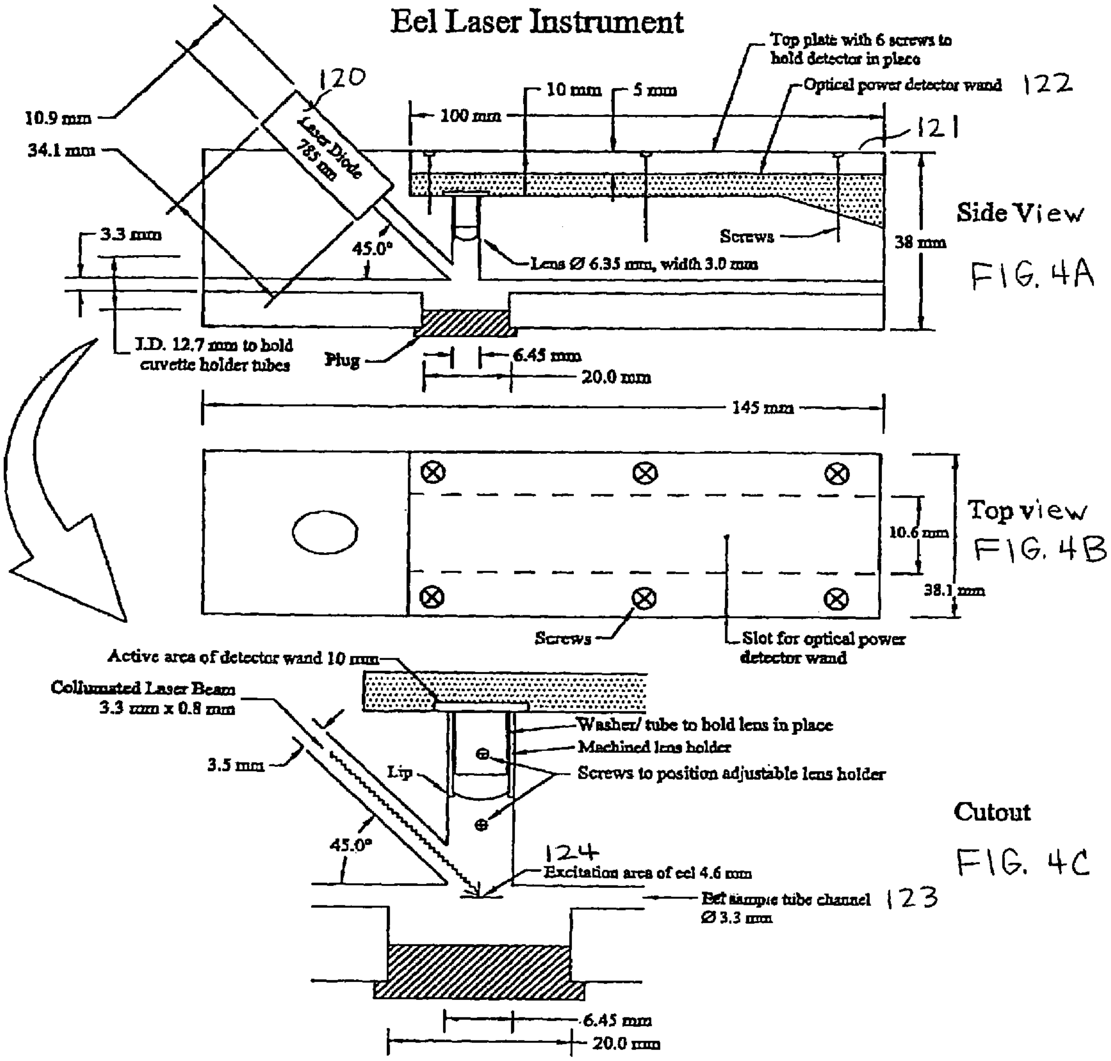
Eel Laser Instrument
Top plate with 6 screws to hold detector in place
Optical power detector wand 122
10 mm
5 mm
100 mm
120
Laser Diode 785 nm
121
10.9 mm
34.1 mm
3.3 mm
45.0°
Screws
Lens Ø 6.35 mm, width 3.0 mm
38 mm
Side View
FIG. 4A
I.D. 12.7 mm to hold cuvette holder tubes
Plug
6.45 mm
20.0 mm
145 mm
10.6 mm
38.1 mm
Top view
FIG. 4B
Screws
Slot for optical power detector wand
Active area of detector wand 10 mm
Collimated Laser Beam 3.3 mm x 0.8 mm
Washer/ tube to hold lens in place
Machined lens holder
Screws to position adjustable lens holder
3.5 mm
Lip
45.0°
Cutout
FIG. 4C
124
Excitation area of eel 4.6 mm
Eel sample tube channel Ø 3.3 mm 123
6.45 mm
20.0 mm

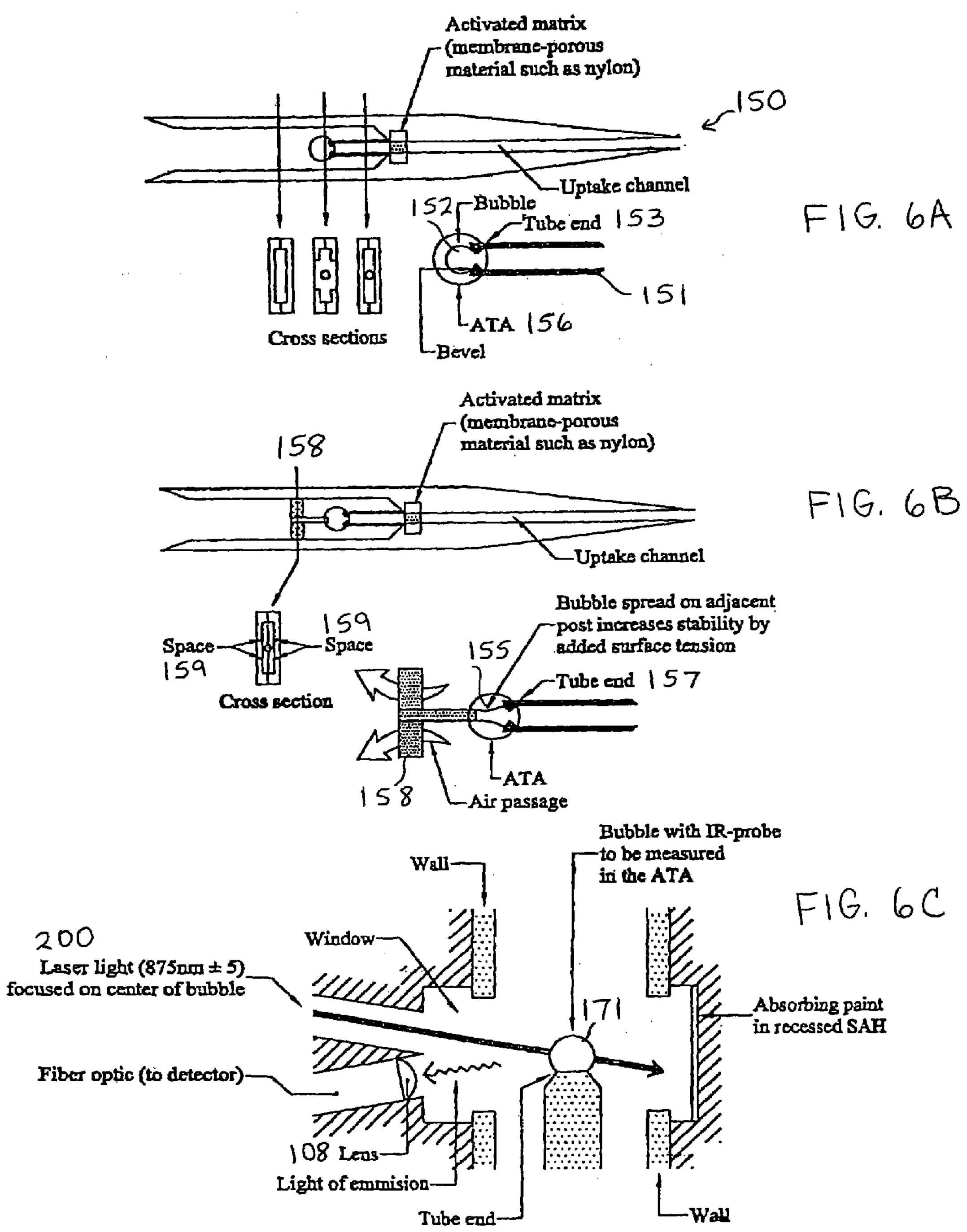
Activated matrix
(membrane-porous
material such as nylon)
150
Uptake channel
152 Bubble
Tube end 153
151
ATA 156
Cross sections
Bevel
FIG. 6A
Activated matrix
(membrane-porous
material such as nylon)
158
Uptake channel
FIG. 6B
Bubble spread on adjacent
post increases stability by
added surface tension
159
Space
Space
159
Cross section
155
Tube end 157
ATA
158
Air passage
Bubble with IR-probe
to be measured
in the ATA
Wall
FIG. 6C
200
Window
Laser light (875nm ± 5)
focused on center of bubble
171
Absorbing paint
in recessed SAH
Fiber optic (to detector)
108 Lens
Light of emmision
Tube end
Wall

MOLECULAR TAG READER

FIELD OF THE INVENTION

The present invention relates to a hand-held electro-optical system which can rapidly read small quantities of selected molecular tags in tissues of animals.

BACKGROUND OF THE INVENTION

There has long been a desire to develop a universal system for detecting molecular species found in biological fluids or synthetic chemical environments. Currently there are a variety of specialized instruments, all of which are large, cumbersome, relatively slow, and expensive to operate, requiring a highly skilled staff.

Two of the most commonly used techniques for measuring the presence and quantity of an analyte in a test sample are ELISA and RIA.

There are many different types of ELISA procedures. The most general format consists of depositing the antigen of choice at a specific concentration in a 96 well plastic plate. The antigen solution is incubated in the plate for one hour before excess antigen is washed out. The plate is then coated with antigen, but the remaining electrostatic charges on the plate must be blocked with a protein buffer for another hour so that test proteins and reagents, which are added later, do not non-specifically bind to the plate. The plate is washed once again before adding the test samples and incubated for another hour. This cycle of washing is repeated and an enzyme labeled anti-ligand is added and incubated for one more hour. Once this last incubation is finished, the plate is thoroughly washed and the enzyme substrate is added. If enzyme is present, the substrate will be converted to product. A colorimetric change occurs which is measured by suitable instrumentation. The data are then expressed on a computer screen or printed by a printer. In some ELISAs, the sample preparation may take as much as an entire day before a reading can be taken.

An RIA is usually more sensitive than an ELISA. The probe used is radioactive and requires special disposal facilities. The sequence steps of the assay are the same as the ELISA, but the probe binds directly to the target molecule without enzymatic conversion of a substrate to a colored product. In a competitive RIA, the radioactive probe and the non-radioactive molecule of interest found in the test sample compete for a common binding site. The gamma and beta radioactive counters used to detect the radiation are large table top or floor model instruments that print out data.

Other techniques and complementary instruments are used for detecting biomolecules, including PANDEX, TDX, HPLC (high performance liquid chromatography), PHAST, GC (gas chromatography), FACS, and others.

Unfortunately, none of the above assays is capable of providing a rapid, reliable identification of fish or other animals rapidly and accurately as to their age, origin, and any experimental protocols to which they have been subjected. Presently available methods are cumbersome (e.g., wire tags), lethal (e.g., otolith marks and wire tags), expensive, and technically demanding (e.g., rare earth metals and genetic testing). All of these methods are time consuming, and most are too large to use with very small fish.

SUMMARY OF THE INVENTION

It is an object of the present invention to overcome the aforesaid deficiencies in the prior art.

It is another object of the present invention to provide a tool to identify stocks of fish or other wildlife without endangering them.

It is another object of the present invention to provide a method and apparatus for quick and easy identification of marked fish or other animals.

It is a further object of the present invention to provide a device that can be used in the field environment to identify fish and other animals rapidly and accurately as to their age, origin, and experimental protocols to which they have been subjected.

It is another object of the present invention to provide a means for identifying commercial livestock herds.

It is yet another object of the present invention to provide a means for identifying valued animals such as horses and dogs.

According to the present invention, a hand-held portable device is provided which can rapidly read small quantities of selected molecular tags in tissues of fish or other animals in the field. The device is composed of four components:

(1) a light source, such as a laser diode;

(2) a sample holder;

(3) an optical system, made of a fiber optic lens and a bandpass filter; and (4) a photo diode detector coupled to an LCD.

The optical system can be modified to eliminate the fiber optics and bandpass filter.

The laser may be replaced by a miniature light bulb coupled to an extra bandpass filter to eliminate lower light wavelength that might interfere with the sensitivity of the instrument. The light sources and other systems can be battery operated.

The optical system is optimized for the type of tag used in the marking procedure. Settings for the optical system are selected based upon the dyes used for tagging. Multiple dyes in one organism can be tested by changing the excitation wavelength and emission measurement settings.

BRIEF DESCRIPTION OF THE DRAWINGS

FIG. 4A shows a side view of an instrument designed for detecting molecular markers in eels.

FIG. 4B shows a top view of an instrument designed for detecting molecular markers in eels.

FIG. 4C shows a cutout view of an instrument designed for detecting molecular markers in eels.

FIGS. 6A, 6B, and 6C show a device in which detection is accomplished without an immobilizing matrix or reaction vessel wall.

DETAILED DESCRIPTION OF THE INVENTION

Figure 1:
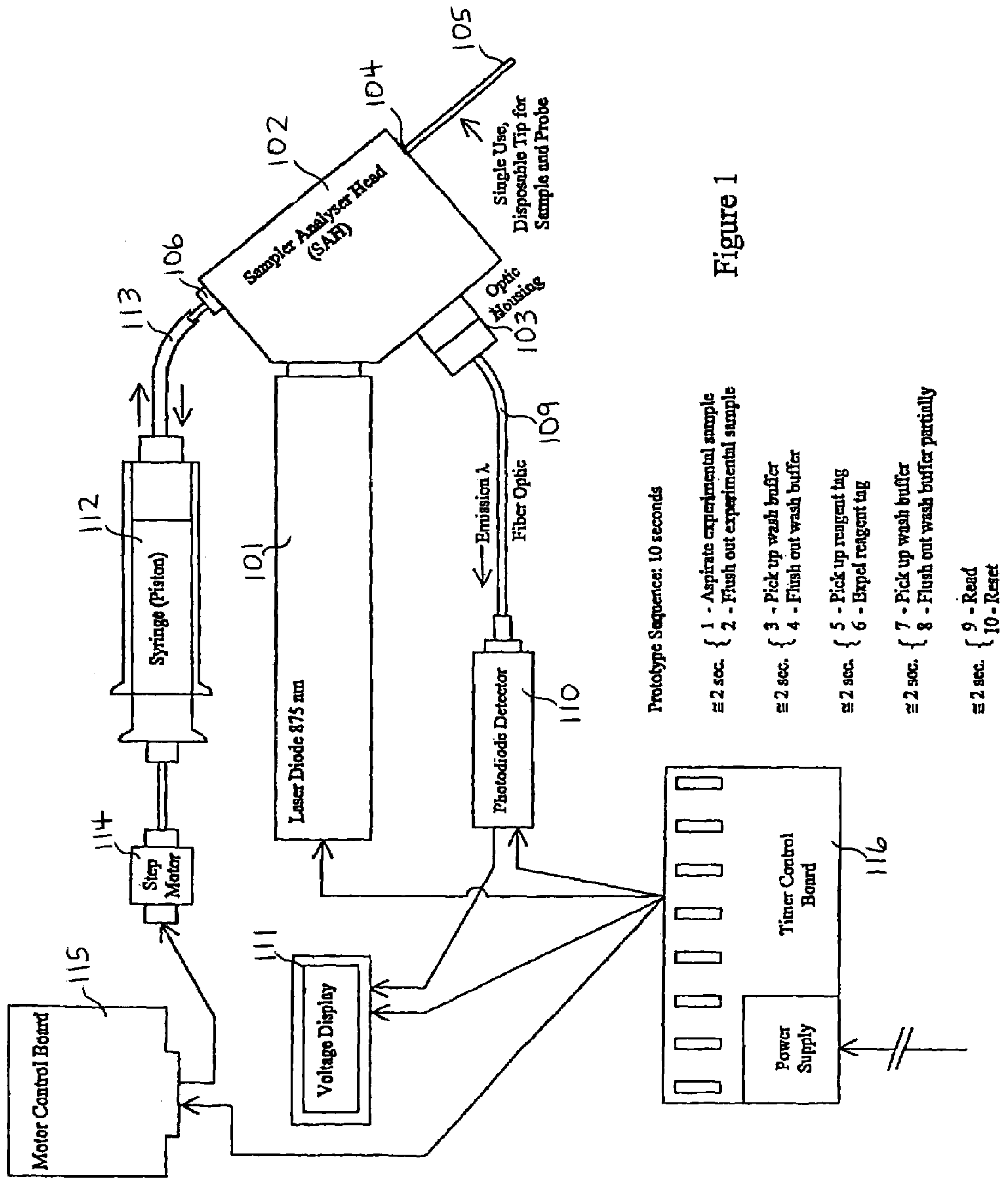
FIG. 1 shows a device according to the present invention for detecting molecular markers.

As shown in FIGS. 1, 2A, 2B and 3, a small (0.5 W) laser diode 101 with an emission wavelength of 785 nm±5 nm operating on its own 6 volt power supply is mechanically coupled to the sampler analyzer head 102. The sample analyzer head 102 is a block of machined hard aluminum or Teflon PTFE, which holds the optic housing 103, the bore 104 for the disposable tip or tube 105, and a negative/positive pressure connecter 106. The optic housing 103 includes a narrow band pass filter 107 of 850±25 nm and a plano convex lens 108, which may be made of BK7 glass. The optic housing 103 is linked through a fiber optic 109 to a silicon photo diode-amplifier 110 with a spectral peak of 740±50 nm, which is wired to an LCD voltage display 111 of 0.05% accuracy in 1 volt increments.

The pressure connector 106 of the sample analyzer head 102 is attached to a stepper motor syringe (piston) assembly 112 with a short tube 113. The electrical power for the stepper motor 114 is activated by a motor control board 115 with a variable speed control switch. The total system is synchronized by a master power and an electronic timer control board 116. The photo diode 110 can be replaced by a photon counting module for more sensitive emission measurements.

Figure 3:
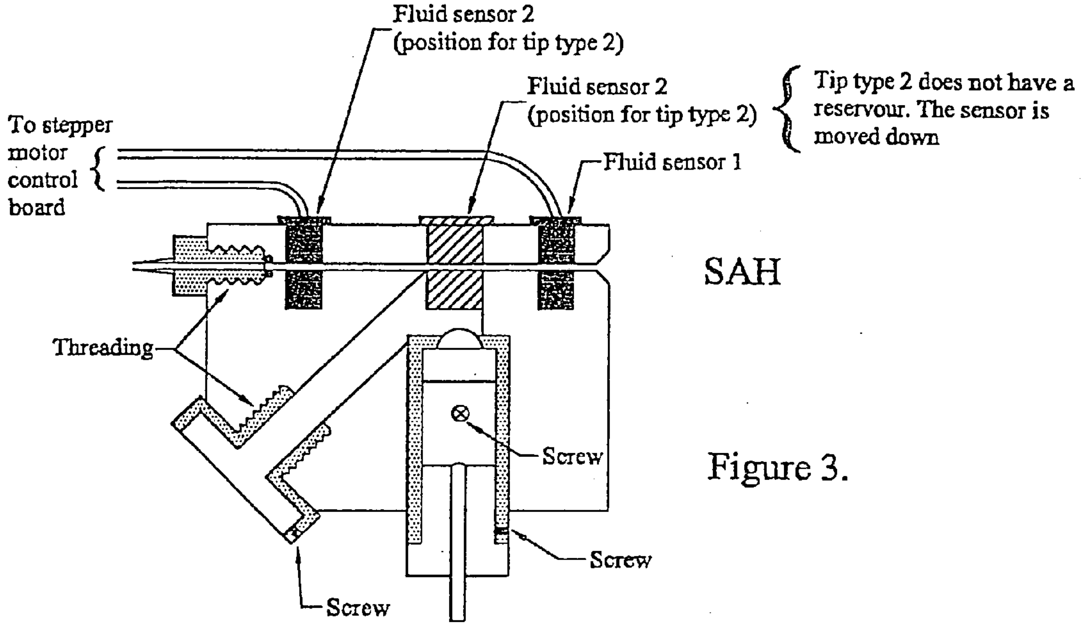
FIG. 3 shows a second embodiment of a sample analyzer head.

As shown in FIG. 3, the level of fluid in the reservoir and uptake channel is determined by timers or by two miniature sensors 117 (sonic) in the sampler analyzer head which are connected to the stepper motor board 115.

FIGS. 4A–4C show another embodiment of the present invention which can be used for monitoring eels. In this embodiment, an eel is introduced into the eel sample tube channel 123 and subjected to light from a laser diode 120, the wavelength of the laser depending upon the fluorescent dye used. The sample analyzer head and the detector are in one block, 121, which comprises the optical power detector wand 122 that attaches to a hand-held optical power meter (not shown). The wand should read in a narrow or specific wavelength corresponding to the wavelength emitted, or with a narrow band bass filter set, or mechanism that would select specific wavelengths before its detector window, since the wand can be calibrated to measure only light emitted at a predetermined wavelength, depending on the fluorescent dye used. This can be done with a narrow pass filter grading system or the like.

The detector measures the light emitted from the laser dye in the fish in microwatts. An increase in the microwatt readings corresponds to an increase in the amount of light emitted, and hence corresponds to a set amount of laser dye in the sample or fish tested.

The eel sample tube channel 123 can have varying diameters to accommodate various size of fish. The eel sample tube channel 123 is manufactured with a large diameter that can be reduced by inserting a series of tubes with smaller internal diameters to accommodate the correct sample size.

Eels passing through the sample tube channel 123 can be counted by breaking a light path 124 as they flow through the channel. The electric eye is placed at the entrance of the sample analyzer head 121. Eels flowing through the tubing can activate the instrument.

Detection Methods

To detect animals, the laser dye is coupled to a labeling molecule such as an antibody or a specific ligand such as avidin, Protein A, Protein G, various antigens, or solid materials such as ion exchange resins, latex beads, or other inert non-fluorescent structures, and use this labeled compound as the reagent tag, i.e.,

DYE+LABELING MOLECULE OR SOLID MATERIAL=REAGENT TAG

The standard detection techniques are then carried out as described in FIGS. 1–5. FIG. 6 is a special application in which detection is accomplished without the interference of any immobilizing matrix or reaction vessel wall. This special detection system eliminates any background emission from materials other than the tag, and hence it is more sensitive than the matrix dependent method. By lowering the background to near zero, the measurements are more accurate and precise since they do not depend on the quality of materials used in the production of disposable tips. The results are expressed in positive values rather than the negative correlations seen in competitive radioimmunoassays (RIA's). In a competitive RIA system, the amount of radioactive label seen or counted decreases as the target molecule being detected increases. In the Near Infrared Molecular Assay (NIRMA) of the present invention, an increase in level or concentration of the target molecule directly corresponds to an increase of dye, and hence an increase in light emission.

The Reagents

Among all spectrofluorescent methods, laser fluorimetry is the most sensitive (1–6). Sauda et al., (1986) demonstrated detection of $10^{-12}$ M laser dye with a 3 nW laser. Also, there are over 2000 laser dyes commercially available (7) from which one can choose to develop a practical detection system. Therefore, a diode laser, a photo diode, and a laser dye must match in order to make the detection system workable.

Since most biological and other materials do not fluoresce between 700 and 1300 nm (4), it was important to find a useful laser dye in that range which could bind to a specific carrier or labeling molecules and act as a tag without losing its fluorescent properties.

Dyes for use in the present invention must have at least the following characteristics:

(1) must fluoresce between 700 and 1300 nm
(2) must be soluble in water
(3) must be non toxic
(4) must be stable when coupled to proteins including during cold storage
(5) must bind electrostatically to specific proteins such as albumin, lipoproteins, and gamma globulins.

While polymethine dyes have an absorption range between 600 and 900 nm (4), most are positively charged and thus are not very useful for directly labeling proteins unless the proteins are negatively charged. Some laser dyes, such as IR-125 and IR-144, are negatively charged, and hence ideal for labeling positively charged proteins (8). A new dye, NN382, can also be used since it has good labeling characteristics.

NN382 has been found to be particularly useful for use in molecular marking of animals. This dye has the following formula:

NN 382

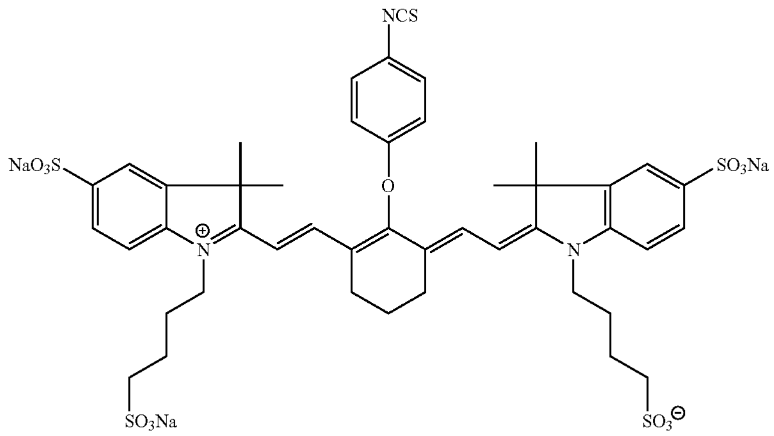

The molecular formula of NN382 is $C_{45}H_{48}N_3O_{13}S_5Na_3$, the compound has a molecular weight of 1067.

The laser dye NN382 has the following characteristics:

(1) absorption maximum of 778 nm
(2) emission maximum of 806 nm
(3) soluble in DMSO and related organic solvents
(4) soluble in pure water
(5) polymerizes and quenches at high temperatures
(6) non toxic
(7) can be stored frozen for long term storage
(8) stable when coupled to proteins and stored in the cold (below 5° C.) and
(9) binds electrostatically to specific proteins such as albumin, lipoproteins, and gamma globulins.

Because wildlife that is to be detected using the system of the present invention is by definition outdoors, the system, including dyes used therein, must be operable under a variety of conditions and at least from about 5° C. to about 20° C. For purposes of the present invention, "cold" refers to temperatures below about 5° C. Of course, the temperatures at which assay are conducted depends on the type of sample used. Water-based samples are generally assayed at temperatures above about 0° C. so that they are in the liquid state.

Disposable Reaction Tips

Figures 5A, 5B, 5C:
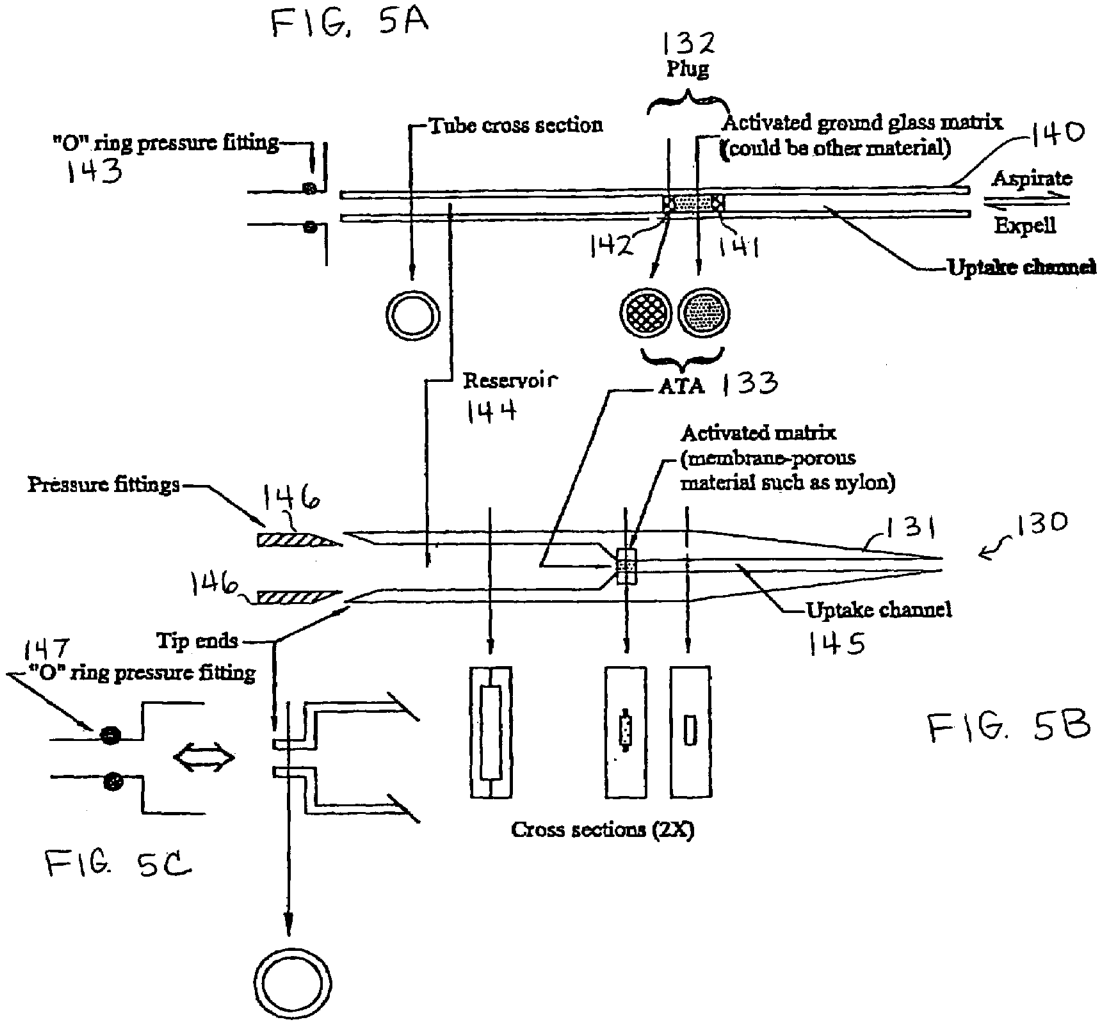
FIG. 5A shows a side view of disposable tip.
FIG. 5B shows a side view of another disposable tip.
FIG. 5C shows a pressure fitting for the disposable tip of FIG. 5B.

The present invention can use two fundamental disposable tip configurations, which are defined by two different types of analysis target area (ATA). The first type, type 1, has an enclosed ATA composed of a solid phase. This type, 130, is shown in FIGS. 5A–5B. The second type, type 2, 150, has an ATA which is solid phase free and not enclosed by materials, as seen in FIGS. 6A–6C.

In tip type 1, 130, the material used for the wall of the disposable tip 131 has a low near infrared excitation/emission profile in the wavelength of interest. One example of a useful material is Teflon FEP, although other materials can be used. Of suitable materials, Teflon FEP is preferred. Many other materials have a higher near infrared background or other less appealing characteristics, such as carrying larger electrostatic charges on the surface and hence attracting and binding biomolecules of interest or reagent tags, which renders the assay less sensitive. The electrostatic charges of the tip must be specially blocked without interfering with the binding characteristics of the plug or matrix, 132. Also, since the tips can be used in a sterile environment, they must be sterilizable. This is preferably effected by radiation, and must not change the properties of any of the materials used in constructing these tips so that the assay is not affected in any way.

The analysis target area (ATA) 133 can be made of micro ground glass, micro glass, or plastic beads, as well as porous nylon matrix, porous composite matrix (e.g., nylon and ion exchange resins) or a fine mesh or screen surface. These materials have the same near infrared, low non-specific binding and sterilizable properties as the FEP housing above. Also, they have an added characteristic, in that they can bind covalently or by other means "target" or "capture" molecules used in the system of the present invention. The target molecules are the chemical structures which are bound to the matrix for the purpose of having specific molecules recognize and bind to them when they are in very close proximity. For example, the target molecule could be an antigen, an antibody, a ligand such as avidin, concanavalin A, protein A, protein G, etc., or a hapten, such as biotin, an enzyme substrate or its product, a chelate, etc. The matrix may not carry any target or captures molecules at first, but these may be supplied in an activated form so that the user can attach any ligand of choice to the matrix.

FIG. 5A shows an FEP tube 140 (24 gauge) with a plug 132 composed of activated ground glass sandwiched between two plastic porous (porex) discs 141, 142. The tube 140 fits into a pressure fitting with an "O" ring 143 to seal the tube.

In FIG. 5B, the reservoir 144 is larger than the uptake channel 145, permitting a bigger sample volume to be collected and tested. In this embodiment, internal pressure fittings 146 are used rather than an external one with an "O" ring 147 as shown in FIG. 5C.

FIG. 6A shows a type 2 disposable tip 150 which has the same external disposition as the tip in FIG. 5B except for a double window in front and back of the ATA 156. Internally, the tip 150 has a small bore tube 151 specially designed to bring a small microliter bubble 152 in front of the detection window. The tube end 153 is designed so as not to touch the internal wall of the tip. Also, by beveling the tube 151, one increases the surface area for better surface adherence of the bubble.

Another embodiment of this design is shown in FIG. 6B in order to flatten out the bubble 155 in which detection occurs. In this embodiment, a post 158 is set close to the tube end 157. In this case, the bubble 155 is hung between the tube end 157 and the post 158, hence increasing the stability of the sample and making surface readings possible with less scatter of the emission wavelength from the reagent tag. A space 159 exists on each side of the post between the post and the internal wall of the tip 160 so that air has access to the uptake channel. When a negative pressure is created, the fluid sample can rise through the uptake channel into the reagent trap and past it to the ATA.

These type 2 disposable tips have a "trap", which is a zone where two competing molecules bind to a matrix. The trap is situated before the end of the specially beveled tube as shown in FIGS. 6A and 6B.

Methods of Operation

Figure 7:
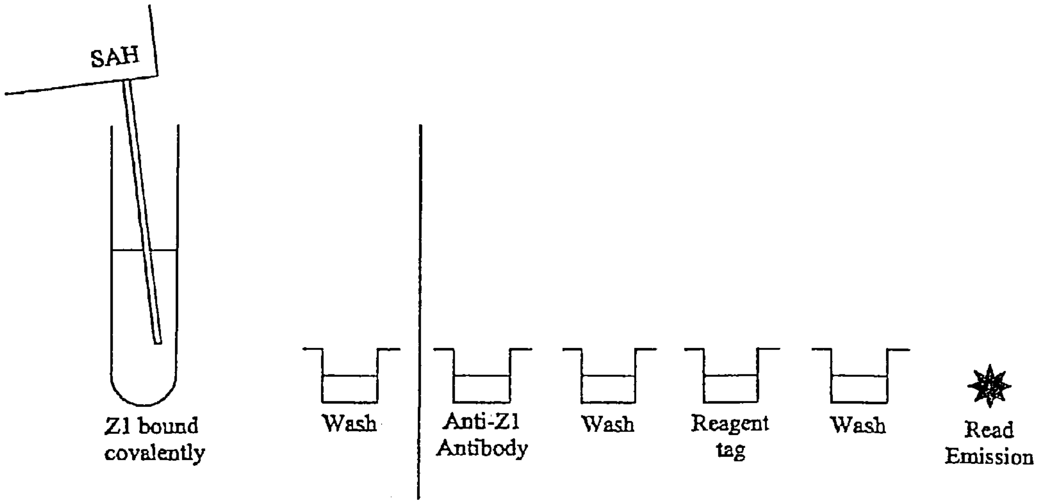
FIG. 7 is a schematic of the process for detecting molecular markers according to the present invention.

FIG. 7 illustrates an antibody determination according to the present invention. A disposable type 1 tip 201 has a specific antigen Z1 bound to its matrix. This is done by using covalent coupling chemistries, although any other means of binding the antibody to the matrix can be used. A fluid sample containing the specific antibody "Z" to antigen "Z1" is aspirated though the uptake channel past the matrix The antibody Z binds to the antigen Z1. Next, the sample fluid is stopped at a predetermined level inside the disposable tip so as not to contaminate the sample analyzer head. The sample is then expelled from the tip. As long as the antigen Z1 is not saturated by an initially high concentration of antibody Z, the antibody Z binds to the antigen Z1 during this phase as long as there is more antibody Z available for binding. A wash buffer is then flowed through the matrix to wash off the sample, as in 3 and 4 above. Next, a specific reagent tag is taken up to a determined level past the matrix. The reagent tag in this case is an antibody tag binding to any antibody Z present. The amount of antibody tag binding to antibody Z determined the intensity of the emission. If no antibody Z is present in the sample, no antibody Z will bind to antigen Z1, and hence no antibody tag will be in the analysis target area once there is no antibody Z to bind to. The reagent tag is expelled. The unbound reagent tag is flushed out of the matrix as above, but the matrix is maintained wet to enhance the reading. The diode laser is fired for a predetermined amount of times and the photo diode picks up the quantity of light emitted by the reagent tag. The voltage generated is amplified and displayed on the liquid crystal display. The number displayed represents a known quantity of antibody Z.

In another embodiment of the present invention, the reagent tag is an avidin tag binding to a biotinylated antibody, which is attached to a specific antibody to the antigen (Ag2) coupled to a solid matrix.

In this embodiment, an antigen determination is conducted. The mechanical sequence of events is identical to those for detecting an antibody. The molecular interactions between antibodies are bound to the matrix rather than to the antigen. This can be effected by direct binding of the antibody to the matrix or through linkers and spacers. One type of spacer molecule is avidin. Coupling of avidin to the matrix, followed by binding of a specific biotinylated antibody Xa as the capturing molecule represent a universal coupling technique useful in antigen detection. This antibody Xa recognizes and captures antigen X2, which is then recognized and bound by a second antibody reagent tag Xb. Diagram 3 illustrates multiple variations of this theme.

In another embodiment, the antigen Ag1 is captured by the matrix bound AG1 specific antibody. The antigen is then recognized and bound by a second biotinylated antibody, which is then bound by the avidin reagent tag.

Antibody or antigen determinations can also be made by reagent tags composed of near infrared probes in or on latex particles, ion exchange resins, or other particulate matter with the appropriate biophysical and chemical characteristics, as shown in Diagram 5.

Figure 2A:
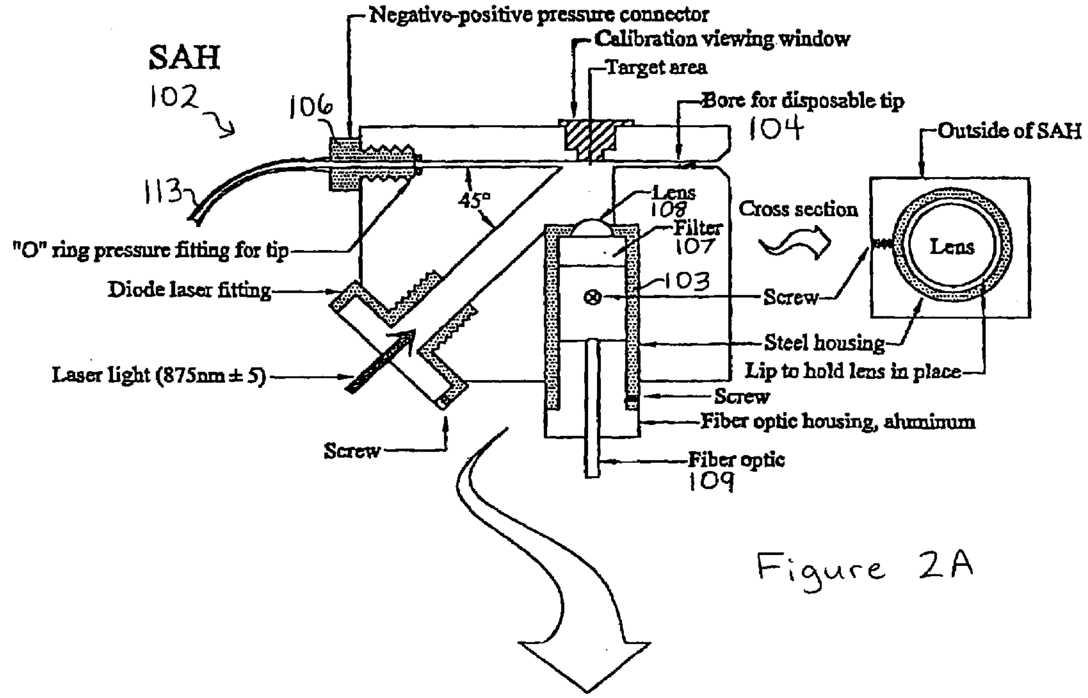
FIG. 2A shows one embodiment of a sample analyzer head.
Figure 2B:
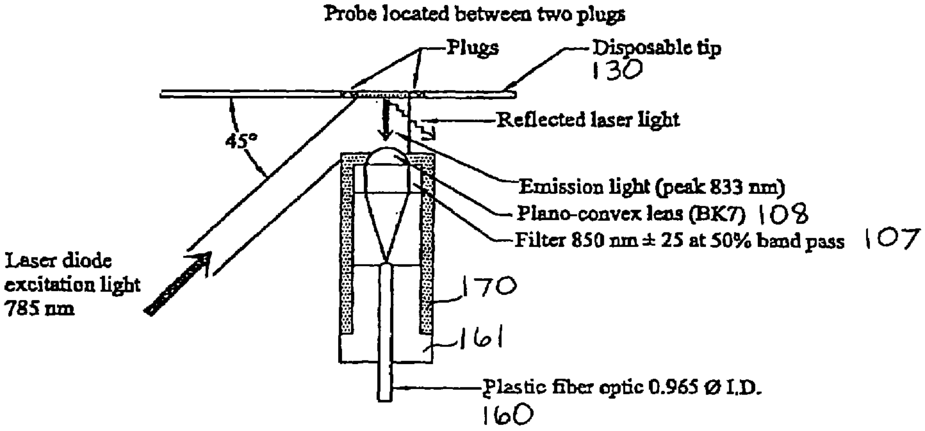
FIG. 2B shows the fiber optic arrangement.

FIG. 2B illustrates detection of emitted light from the reagent tag. The laser diode 101 excites the dye NN 382 at 785 nm, which is very close to the maximum excitation absorbance of the laser dye, i.e., 778 nm. The laser light hits the matrix 132 in the disposable tip 150 at a 45 degree angle, but the detector lens 108 and the filter 107 are at a right angle to the emitting matrix. It is important to note that the matrix 132 is not transparent, and therefore the light must be detected on the same side as the excitation in order to capture most of the signal from the matrix. Also, the excitation angle prevents most of the reflected light from entering the detection system, since it bounces off at a 45 degree angle away from the lens. The filter stops the laser light from entering the optical housing 170 and only lets emission light pass through. The emitted light from the dye on the matrix 132 is focused on the end of a fiber optic 160 contained in a fiber optic housing 161 by a plano-convex lens 108 closely situated to the emission source. The closer the lens is to the source, the more light it can capture. A large lens with a short focal length would be ideal. However, if the optical housing 170 is too close to the emission source, it infringes on the laser light path. The optical housing 170 and the sample analyzer head chambers are coated with a black matte non-reflecting or emitting paint.

Assays described above are based upon type 1 disposable tips in which the reagent tag is on a matrix surrounded by the tip wall. Another type of assay is based on type 2 disposable tips, which increases the sensitivity and decreases error in the assay.

With a type 2 tip, a ligand is coupled to the matrix, which ligand specifically binds the molecule of interest in a test sample as well as the reagent tag. The reagent tag is the same as the molecule of interest but is labeled with a laser dye, such as NN 382. This is a competitive assay in which an antibody b coupled to the matrix specifically recognizes and binds the test sample antigen b1 flowing through the matrix, as well as the reagent tag, antigen b1-NN 382. In order to measure the amount of antigen b1 in a test sample, a calibrated quantity of reagent tag is mixed with the test sample. The amount of reagent tag added to the test sample is just enough to saturate all of the matrix bound antibody b binding sites when no other competitive antigen to the reagent tag is present in the sample being tested. Hence, no excess reagent tag flows through the matrix, as it is all captured by the antibody on the matrix and appears in the ATA, giving a zero reading. The only means by which the reagent tag appears in the ATA is when the reagent tag and antigen b1 from the test sample are mixed. Test sample antigen b1 competes against the reagent tag for the same binding site of antibody b located on the matrix, and therefore some of the reagent tag is not bound to the matrix. The free reagent tag flows into the ATA, where it is measured.

As increasing amounts of test sample antigen are present in the mixture, more and more of the reagent tag appears in the ATA. This method shows that, with a very low concentration of test sample antigen b1, one obtains low readings, while, with equal amounts of reagent and test antigen b1, half the reagent will appear in the ATA bubble. Finally, when high concentrations of antigen b1 are tested, most of the reagent tag will be found in the ATA. Graphic representation of the NIRMA vs. RIA is shown as the last part of diagram 6. In the NIRMA graph, it can be seen that as the concentration of antigen in the sample rises, the reagent tag readings increase proportionately. In the standard competitive RIA, the converse is true: as the concentration of the antigen in the sample increases, the amount of radioactive tag being measured decreases. RIA requires generation of a standard curve, while NIRMA does not, since it is established that a certain amount of antigen binding the matrix will displace an equal amount of reagent into the ATA.

Details of measurements taken in the ATA of the disposable tip type 2 can be seen in FIG. 6C. The exciting laser light 200 is focused in the center of the bubble 171, which is the ATA, while the emission wavelength from the bubble is captured by the detector lens 108 without any interference from building materials used in making the tip.

When using the eel laser instrument, shown in FIG. 4, the eel (not shown) is passed through the eel sample tube 123. The eel is aligned with the ATA, the laser is fired, and the amount of dye in the eel is measured from its emission by the optical detector wand 121. The results are expressed in mW.

Near infrared molecular assay, or NIRMA, provides speed of operation, in which animals can be detected in seconds versus hours of days. The assay can be used with small samples, from less than about one microliter, to about 1000 microliters. The assay is non-isotopic and non-enzymatic, and uses a small, portable, hand held tool which can be battery operated. There is no fluorescent background because of the selection of the near infrared range of the reagent tag. The assay is highly sensitive, because of the use of near infrared, two types of tips, and the electro-optic designs. There is no requirement for precalibration or for providing a standard curve. The system is intuitive, and little training is required. The assay can be used under sterile and non-sterile conditions. By selecting the tip and optical system used, the assay can be adapted to low concentrations of molecules in a test sample. Compared to other methods for detecting animals, the method of the present invention is not expensive. The tags cannot be removed by poachers, and the assay system can be used to encode complex information over long periods of time, i.e, years.

The foregoing description of the specific embodiments will so fully reveal the general nature of the invention that others can, by applying current knowledge, readily modify and/or adapt for various applications such specific embodiments without departing from the generic concept, and, therefore, such adaptions and modifications should and are intended to be comprehended within the meaning and range of equivalents of the disclosed embodiments. It is to be understood that the phraseology or terminology employed herein is for the purpose of description and not of limitation.

REFERENCES

1. Baker, K. J., "Binding of sulfobromophthalein (BSP) sodium and indocyanine green (ICG) by plasma O 1 liproproteind" P.S.E.B.M. 122:957 (1966)
2. Birge, R. R., "Kodak laser dyes" Kodak Publication JJ-169 (1987)
3. Diebold, G. J., et al., "Laser fluorimetry:subpicogram detection of aflatoxins using high-pressure liquid chromatography" Science 196:1439 (1977)
4. Sauda, K., et al., "Determination of protein in human serum by high-performance liquid chromatography with semiconductor laser fluorometric detection" Anal. Chem. 58(13): 2649 (1986)
5. Imasaka, T., et al., "Semiconductor laser fluorimetry in then near-infrared region" Anal. Chem 57(7):1077 (1984)
6. Lidofsky, S. D., et al., "Laser fluroscence immunoassay of insulin" Anal. Chem. 51(11):1602 (1979)
7. Organic Chemical List. Nippon Kanko-Shikiso Kenkyusho Okayama 1969 (supplement 1974)
8. Zare, R. N. "Laser chemical analysis" Science 226:298 (1984)

What is claimed is:

1. An apparatus for detecting a target molecule in a sample fluid in vivo or in vitro, comprising:

an uptake channel enclosed by a wall and having a receiving end to receive the sample fluid;

a matrix within the uptake channel, the matrix having a capture molecule for the target molecule immobilized therein;

an inner tube connected to the matrix opposite the receiving end of the uptake channel;

a reservoir on a side of the matrix opposite the receiving end of the uptake channel, and formed by a wall extending from said wall of said uptake channel, said reservoir wall further extending beyond and surrounding said inner tube;

an analysis target area in said reservoir extending from an end of the inner tube opposite the matrix, wherein a bubble from the sample fluid can be formed therein;

a reagent tag that binds to the target molecule and fluoresces when subjected to near-infrared light emissions;

a light source focused directly on the analysis target area where the bubble is formed, the light source configured to emit light in a wavelength comprising near-infrared light emissions; and a detector configured to detect the reagent tag that fluoresces within the analysis target area when subjected to the light source.

2. The apparatus according to claim 1 wherein the light source is a laser diode.

3. The apparatus of claim 1 wherein the detector comprises a fiber optic lens and a bandpass filter.

4. The apparatus according to claim 1 wherein the detector comprises a photodiode coupled to an LCD.

5. The apparatus of claim 1 wherein the matrix comprises one of micro-ground glass, micro-glass, plastic beads, nylon, a mesh, and a screen, and the matrix has physical barriers on opposite sides thereof.

6. The apparatus according to claim 1, wherein the reagent tag comprises a laser dye.

7. The apparatus according to claim 6, wherein the laser dye is soluble in water and binds electrostatically to one or more of albumin, lipoproteins, and gamma globulins.

8. The apparatus according to claim 7, wherein the laser dye comprises a negative charge.

9. The apparatus according to claim 8, wherein the laser dye has the formula $C_{45}H_{48}N_3O_{13}S_5Na_3$.

* * * * *